United States Patent [19]
Kaye et al.

[11] Patent Number: 5,614,726
[45] Date of Patent: Mar. 25, 1997

[54] AUTOMATED OPTICAL ALIGNMENT SYSTEM AND METHOD USING RAMAN SCATTERING OF CAPILLARY TUBE CONTENTS

[75] Inventors: Wilbur I. Kaye, Princeville, Hi.; Stephen L. Pentoney, Jr., Yorba Linda, Calif.

[73] Assignee: Beckman Instruments, Inc., Fullerton, Calif.

[21] Appl. No.: 409,557

[22] Filed: Mar. 23, 1995

[51] Int. Cl.[6] .......................... G01N 27/00; G01N 21/31; G01N 21/01; G01N 27/447
[52] U.S. Cl. .......................... 250/574; 204/452; 204/603; 422/82.08; 422/82.05; 356/246
[58] Field of Search ....................... 250/574, 575, 250/576, 206.1, 206.2, 227.29; 356/244, 246, 319, 344, 411, 434, 436; 204/180.1, 182.8, 183.3, 299 R; 422/82.05, 82.08, 82.09

[56] References Cited

U.S. PATENT DOCUMENTS

| | | | |
|---|---|---|---|
| 4,088,407 | 5/1978 | Schoeffel et al. | 356/317 |
| 4,188,542 | 2/1980 | Hogg et al. | 250/458 |
| 4,273,443 | 6/1981 | Hogg | 356/343 |
| 4,657,397 | 4/1987 | Oehler et al. | 356/414 |
| 5,208,466 | 5/1993 | Pentoney, Jr. | 250/574 |
| 5,292,483 | 3/1994 | Kaye | 250/458.1 |
| 5,430,541 | 7/1995 | Sapp et al. | 356/246 |
| 5,471,299 | 11/1995 | Kaye et al. | 356/336 |
| 5,484,571 | 1/1996 | Petoney, Jr. et al. | 422/82.08 |

*Primary Examiner*—Edward P. Westin
*Assistant Examiner*—John R. Lee
*Attorney, Agent, or Firm*—William H. May; Janis C. Henry

[57] ABSTRACT

A system and method are disclosed for optically aligning a capillary tube and an excitation laser beam for fluorescence detection applications by utilizing the Raman scatter signals of the capillary tube's contents. For example, Raman scatter by an electrophoretic separation matrix may be used for alignment in a capillary electrophoresis system. Fluorescent material may be present and may also be used for alignment purposes, but is not necessary. The invention employs a parabolic reflector, having apertures through which the capillary tube and the laser beam are guided so that they intersect, preferably at right angles and at the focal point of the reflector. The Raman scatter signals of the material within the capillary tube are collected via a series of filters and this information is used to reposition, if necessary, a focusing lens that directs the excitation beam into the reflector and the capillary tube, so that the Raman scatter signals are maximized. Maximal Raman scatter signals indicate proper alignment of the capillary tube and the excitation beam. Other signals, such as fluorescence emission from the sample, may then be gathered. Adjustment of the focusing lens may be automated so that alignment of the capillary tube and the beam is maintained throughout analysis of the tube's contents. Sequential alignment of an array of capillary tubes with an excitation beam is also disclosed.

48 Claims, 8 Drawing Sheets

AUTOMATED OPTICAL ALIGNMENT SYSTEM AND METHOD USING RAMAN SCATTERING OF CAPILLARY TUBE CONTENTS

BACKGROUND OF THE INVENTION

1. Field of the Invention

This invention relates to optical analysis of the contents of capillary tubes or other small separation channels.

2. Description of Related Art

Laser-induced fluorescence detection is an important optical detection technique for the analysis of biological samples, such as macromolecules that are subjected to capillary electrophoresis. Because capillary tube dimensions and laser detection volumes are extremely small in the capillary tube fluorescence context, however, proper optical alignment of the capillary tube detection volume with respect to the fluorescence excitation source is critical. Maximum sensitivity is achieved only when the entire optical train is properly aligned. Typically, the excitation source is focused into a narrow band of ≦100 microns, which illuminates a small detection region of the capillary tube. Not only is it difficult to correctly position the capillary tube in the excitation source light path, but it is also difficult to maintain this position once it is achieved. This is due in part to shifting of the tube under the stress of high field strength or thermal variations in the environment. It is also a result of the requirement that capillary tubes be readily replaceable.

A common method for accomplishing alignment entails filling the capillary tube with a fluorescent solution and adjusting the tube-and-beam intersection while monitoring the fluorescence with a detector, such as a photomultiplier tube or a photodiode to achieve a fluorescence intensity maximum. This technique is only relevant for open-tube applications, however, such as capillary zone electrophoresis, since the fluorescent solution is not easily removed from gel-filled tubes that will be used for electrophoresis of samples. Even so, it is generally undesirable to insert fluorescent material into any separation tube for alignment or other control purposes, because adsorption of fluorescent material residue on the tube walls may interfere with the analysis of samples. Furthermore, this method does not allow for dynamic alignment during analysis.

U.S. Pat. No. 5,208,466, commonly assigned, discloses an apparatus and method for aligning a capillary tube with respect to a laser beam source for fluorescence detection. That invention employs photosensors to detect the light reflection and scatter patterns originating from the walls of the capillary tube and utilizes the symmetry of those scatter patterns to indicate optimum alignment. The photosensors may also provide a means of feedback control.

It is an object of the present invention to provide a simple, precise means for alignment of a capillary tube's contents with a detection optics path, both in static and fully-automatable dynamic modes. For economic purposes, the invention should employ a minimal number of detectors. It is a further object to effect alignment without the need to introduce fluorescent material into the capillary tube.

DISCLOSURE OF THE INVENTION

The above objects may be achieved through an automated system and method for aligning a capillary tube at a desired location with a laser beam by utilizing the Raman scatter characteristics of the matrix contained within the capillary tube. Raman scattering is a change in frequency and phase observed as light passes through a transparent medium, such as a capillary electrophoresis separation matrix. Using the ever-present Raman scatter signals of a filled capillary tube is superior to using the transmitted or scattered beams from the sample as these can vary in both intensity and spatial distribution as a consequence of slight imperfections in the wall of the capillary tube. Fluorescent material is not necessary, but may be within the capillary tube's detection region during alignment. A "matrix," as used in this context, may be water, buffer, gel, sample or other material with which the tube is filled.

The invention entails intersecting the capillary tube and the laser beam within an axially symmetrical concave reflector having a focal region, preferably a parabolic reflector, by directing the capillary tube and the beam through guides in the wall of the reflector. Preferably, the capillary tube and the beam intersect at the focal region of the reflector and more precisely at approximately right angles at the focal point of a parabolic reflector. A plano-convex lens positioned outside the reflective wall focuses the beam into the capillary tube. A series of blocks and filters obstructs a substantial portion of the very intense Rayleigh scattering from the interfaces where abrupt refractive index changes occur and also obstructs the reflections surrounding the capillary tube. The blocks and filters permit passage of the Raman scatter signals and any fluorescence emission from the capillary tube's contents. The Raman scatter signals from the capillary tube's contents are detected and then maximized by adjusting the lens. The beam and the capillary tube are thus properly aligned for collection of fluorescence emission or other sample detection signals. Positioning of the lens may be automated using feedback to maintain optical alignment throughout the examination of the capillary tube's contents. Similarly, fluorescence signals from the region of intersection may be used for alignment of the capillary tube and the beam. An array of capillary tubes may also be guided through the reflector and sequentially aligned with the beam.

BEST MODE FOR CARRYING OUT THE INVENTION

Figure 1:
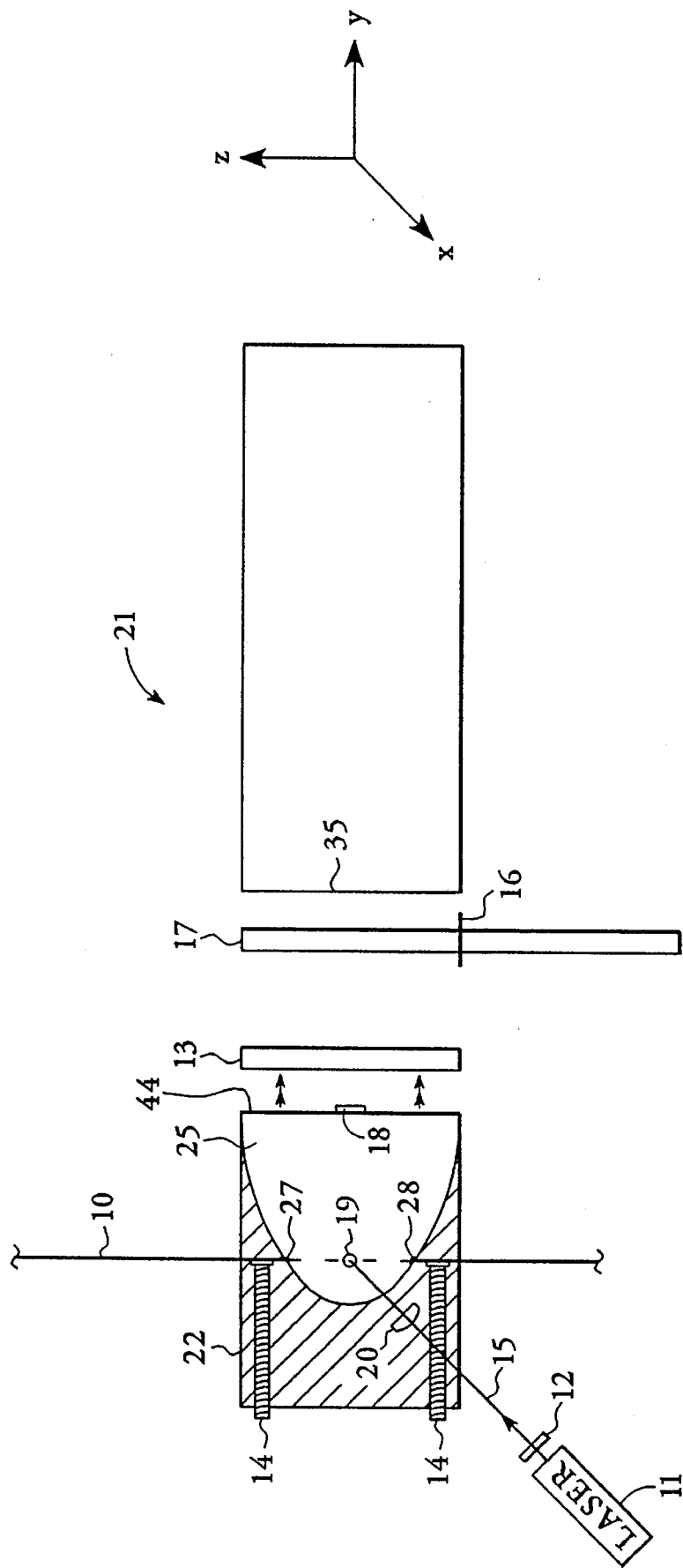
FIG. 1 presents the optical system according to the preferred embodiment of the present invention, with a side view of the parabolic reflector.

With reference to FIG. 1, parabolic reflector 25 is shown in a side view. Reflector 25 is an axially symmetrical concave paraboloid and is shown in fitted holder 22, according to one embodiment. Fitted holder 22 may be a cylindrical body in which reflector 25 is formed, e.g. as a polished paraboloid surface of an aluminum block or a metallized paraboloid mirror surface of a plastic block, or it may be a separate support device shaped to fit the reflector. Other means of supporting reflector 25 may be used.

Figure 2:
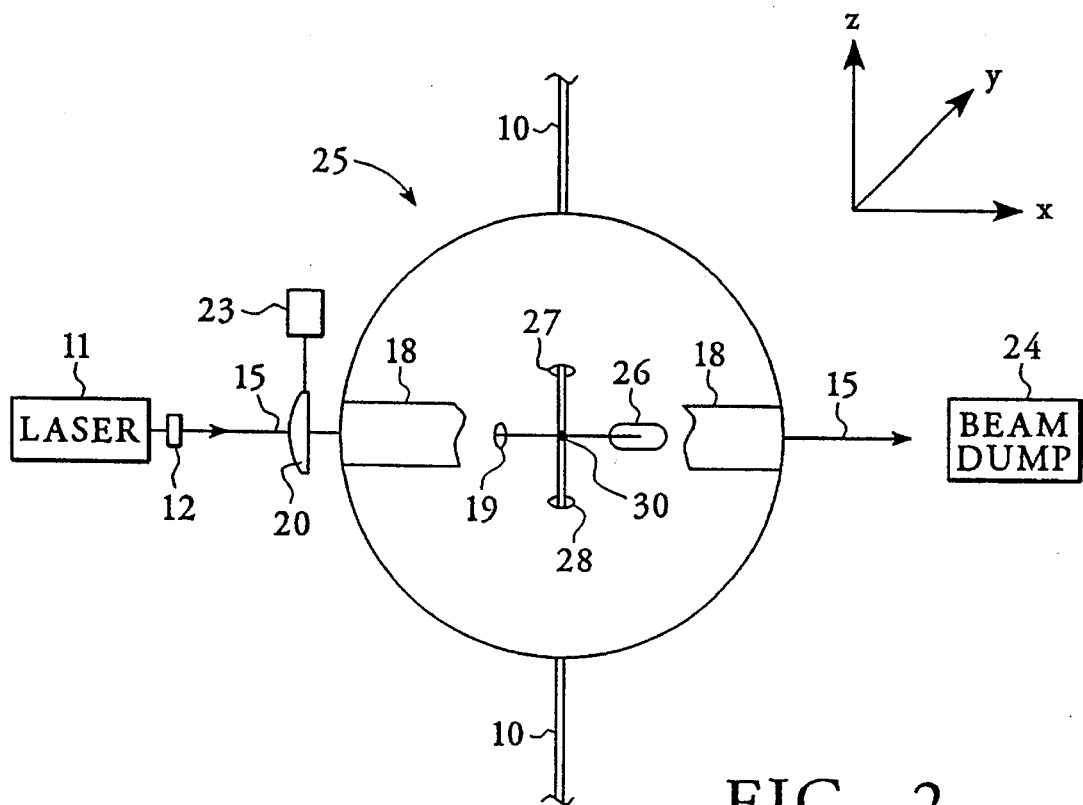
FIG. 2 presents the optical system according to the preferred embodiment of the present invention, with an end view of the parabolic reflector.

Reflector 25 has a wall with a reflective concave interior surface, a first end which is open and is bounded by a rim 44, and an end opposite the rim which has a bowl-shaped region. The bowl incorporates the vertex 43, visible in FIG. 10, which is the point in the bowl that is aligned with the central axis of reflector 25. Reflector 25 also has a focal point 30, as seen in FIG. 2, and thus a focal plane which is the plane that is perpendicular to the central axis of reflector 25 and that passes through the focal point 30. The focal region of reflector 25 thus incorporates a focal plane and focal point 30. A capillary tube 10 and an excitation beam 15 are made to intersect within reflector 25 through the use of guides in the wall 45, shown in FIG. 10, of reflector 25. If a solid holder such as fitted holder 22 of FIG. 1 is used to support reflector 25, openings should be created through the holder for introduction of tube 10, beam 15, and a pair of spring plunger screws 14 which may be desired to hold the position of tube 10.

The position of the guides according to the preferred embodiment of the present invention is more clearly visible in FIG. 2. A set of tube guides, 27 and 28, comprises entrance and exit apertures, respectively, for guidance of capillary tube 10 through reflector 25. A set of beam guides, 19 and 26, comprises entrance and exit apertures, respectively, for excitation beam 15 in the preferred embodiment. The set of tube guides is defined such that the apertures are oppositely-spaced, i.e. approximately 180° apart, near, or preferably at, the focal plane of reflector 25. Similarly, it is preferred that the set of beam guides is defined such that the apertures are oppositely-spaced in the wall at the focal plane. The tube entrance aperture 27 and the beam entrance aperture 19 are approximately 90° apart along the focal plane in the preferred embodiment, i.e. the four holes are approximately equidistant. Therefore, the apertures through the wall of reflector 25 are positioned so that tube 10 and beam 15 intersect at approximately 90° angles within reflector 25, according to this embodiment. "Approximately," as used in reference to the positions of the guides and of the intersection, is meant to preferably include positions within 10° of the given positions.

This point of tube-and-beam intersection preferably coincides with the focal point 30 of reflector 25. In the first illustrated embodiment, tube 10 is inserted through tube apertures 27 and 28 so that tube 10 flies along a Z-axis, visible in FIGS. 1 and 2, and preferably tube 10 falls on the focal point 30 of reflector 25. In this embodiment, beam apertures 19 and 26 are positioned in the wall of reflector 25 so as to cause beam 15 to pass from hole 19 to hole 26 through reflector 25 along an X-axis.

It is also possible to define the guides such that tube 10 and beam 15 intersect at other than right angles. For example, the set of tube guides, 27 and 28, may be defined as in the above embodiment for guidance of tube 10. The position of the pair of beam apertures, 19 and 26, however, may be shifted in the focal plane, relative to the tube apertures, away from the 90° position described above. The position of the beam apertures may also be shifted out of the focal plane. For example, directing beam 15 to intersect tube 10 from an angle above the focal plane may be desired, and the beam apertures should be defined accordingly.

The diameter of beam 15 is less than the diameter of tube 10 at the beam focus, and beam 15 should intersect the center of tube 10 at focal point 30. Excitation beam 15 has its source at laser 11. Beam 15 passes from laser 11 through excitation filter 12 and is then focused by plano-convex objective lens 20. Lens 20 is oriented so that beam 15 enters lens 20 at its convex surface and exits at its planar surface. After passing through lens 20, beam 15 enters reflector 25 at hole 19 in the preferred embodiment.

The intersection of tube 10 and beam 15 causes illumination and excitation of the contents of tube 10. The region of intersection forms a detection region from which emissions including Raman scatter signals and fluorescence signals emerge. The resulting reflections, emission, and scattering are collimated by reflector 25 and directed away from the bowl and toward the open end, due to the parabolic shape of reflector 25. The double arrowheads signify the general path of the emitted signals. Beam aperture 26 may be sized large enough to allow passage of the most intense portion of the transmitted and scattered light in the plane perpendicular to tube 10. Thus, beam aperture 26 is in the shape of a slot having its larger width in the axial direction of reflector 25, as illustrated in FIG. 2, since the transmitted light fans out in a plane perpendicular to tube 10. A beam dump 24 is provided to trap light emerging from beam aperture 26, so that it does not interfere with the detection optics of the system.

Proximate to the rim 44 of reflector 25 lies a scatter block. Scatter block 18 of the preferred embodiment is a narrow strip of opaque material designed to physically obstruct a substantial portion of the Rayleigh scattering and the reflections which surround the tube 10 in a well-defined plane normal to the axis of tube 10. Scatter block 18 is shown in segmented format for purposes of illustration in FIG. 2 and is positioned along the axis of beam 15, which is the X-axis in FIGS. 1–2.

Signals that are not thus blocked then pass to long pass filter 13, which greatly attenuates any remaining Rayleigh scatter and reflections. The remaining signals pass through to bandpass filter wheel 17, which rotates about spoke 16.

Figure 3A:
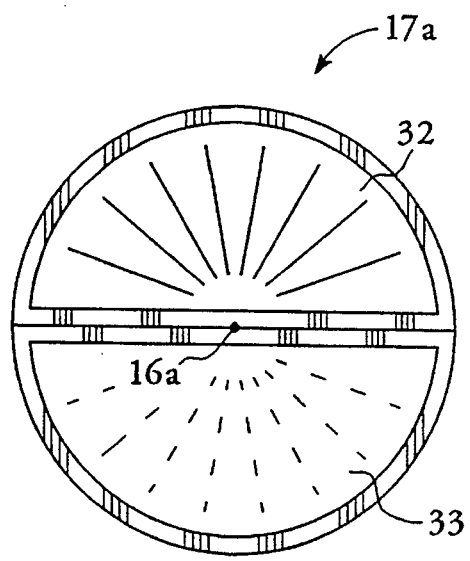
FIGS. 3A–3B show two possible embodiments for the rotating filter wheel of the present invention.
Figure 3B:
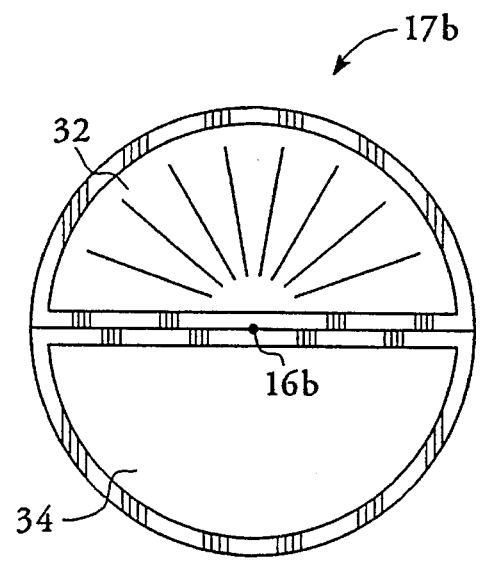

FIGS. 3A–3B illustrate two possible embodiments for filter wheel 17 of the present invention. FIG. 3A has a wheel 17a which has two 180° sectors. Sector 32 is a bandpass filter allowing passage of the desired fluorescence emission signals and sector 33 is a bandpass filter allowing passage of signals indicative of Raman scattering. Alternatively, filter wheel 17 may have two 180° sectors comprising fluorescence sector 32, which is the same as in wheel 17a, and sector 34, which is open, as depicted in wheel 17b of FIG. 3B.

The use of a parabolic reflector, or a similar axially symmetrical concave reflector, to collimate the light reduces the number of optical components necessary for fluorescence detection, makes for efficient removal of scattering radiation by bandpass filters, and simplifies alignment of the beam and tube. This is because proper spectral filtering is best accomplished with irradiation that is normal to the surface of a bandpass filter.

Figure 4:
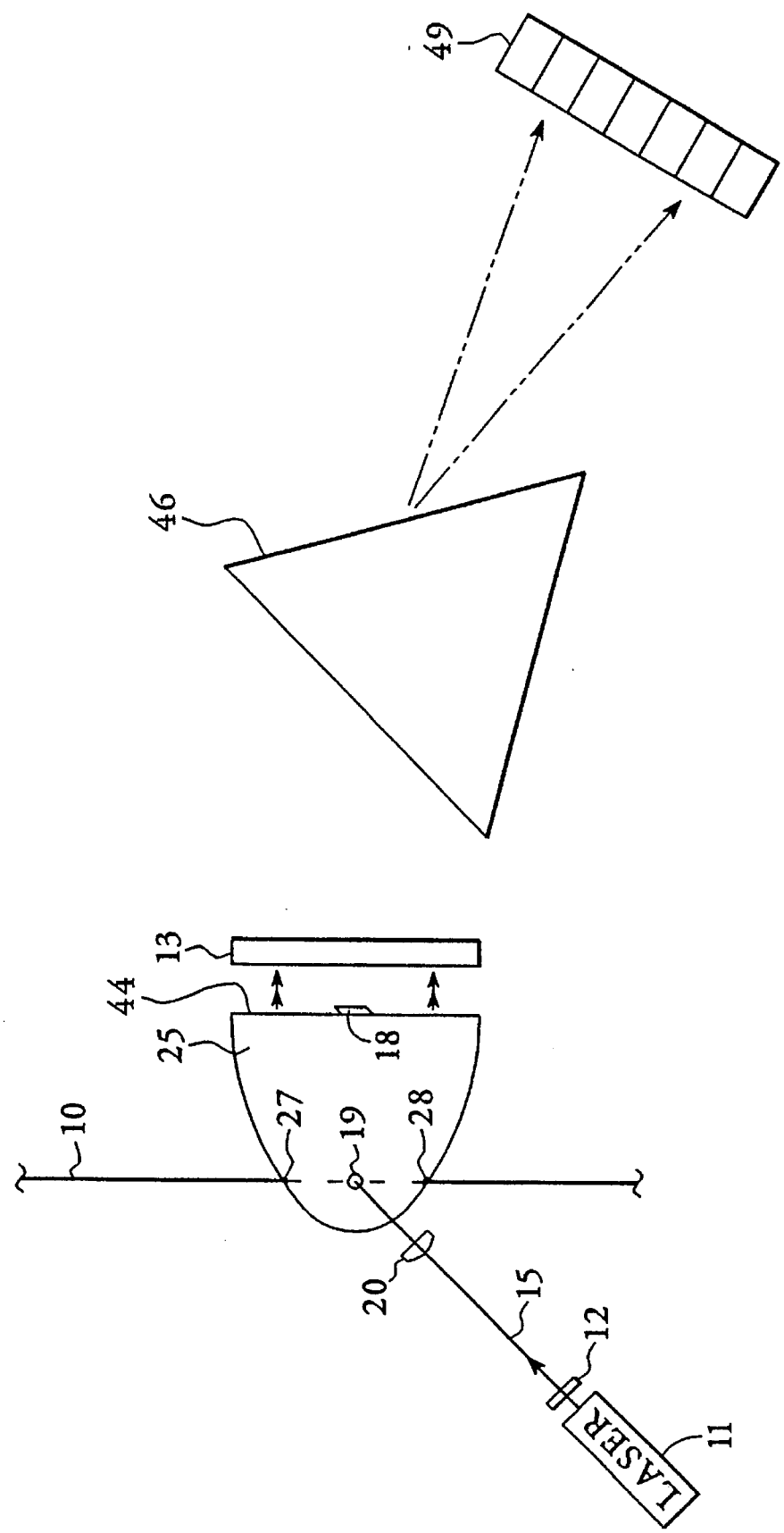
FIG. 4 shows an alternative detection scheme of the present invention.

The signals passing through this series, 18-13-17, of blocks and filters is detected by a detector 21 of FIG. 1, such as a photomultiplier tube. Other means for isolating the spectral region of interest may be substituted. Other detection schemes are also applicable. For example, an array-type detector 49, of FIG. 4, such as a charge coupled device or photodiode array, and a dispersive element 46 for separation of the signals, such as a grating or a prism, may be used. These would allow simultaneous monitoring of Raman scatter and fluorescence emission signals.

The purpose of carefully intersecting beam 15 and tube 10 within parabolic reflector 25 and of collecting and detecting the resulting Raman scatter signals is to effect precise alignment for fluorescence analysis of the sample components within the tube. If the beam and tube are misaligned even slightly, then serious detector and system performance degradation could result. More particularly, if the intersection of beam 15 and tube 10 is displaced from focal point 30 of reflector 25 in the Z-direction, according to the configuration shown in FIG. 1, then the detected beam will not be collimated. As long as the detection window of detector 21 is large, the alignment in this direction is not critical. Preferably, detection window 35 of detector 21, shown in FIG. 1, has a diameter approximately equal to rim 44 of reflector 25.

Alignment in the Y-direction, however, is crucial to the proper functioning of the detection system. To effect proper Y-direction alignment of beam 15 and tube 10, lens 20 of FIGS. 1–2 is shifted, generally either by translation in a Y-direction or rotation about a Z-axis. FIG. 2 shows a positioner 23 in communication with lens 20. This adjustment of lens 20 may be automated so that detection of the Raman scatter signals from the capillary tube's contents provides a feedback to lens 20 and lens 20 is shifted to maximize the Raman scatter signal intensity. This is a means of compensating for any drift of alignment during analysis.

Figure 5:
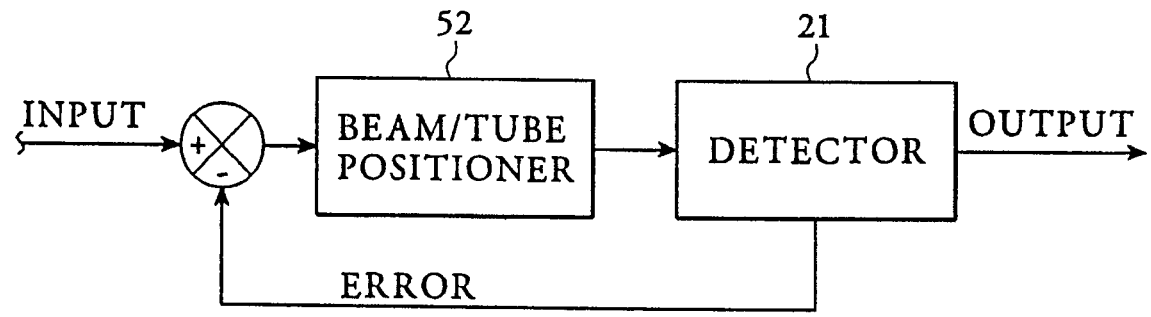
FIG. 5 is a diagram of the feedback mechanism for positioning of the beam and the capillary tube according to the present invention.

For example, FIG. 5 shows a closed loop servo system with a beam/tube positioner 52 that automatically shifts the relative positions of the excitation beam 15 and the capillary tube 10. As stated earlier, shifting of lens 20 with positioner 23 is the preferred method of shifting the relative positions of the beam and the tube. Other means of shifting may be utilized, however, such as shifting the beam with a mirror or mechanically shifting the tube. Beam/tube positioner 52 is in communication with detector 21 which generates an error signal, i.e. feedback, with reference to deviations from a maximum Raman scatter signal found in calibration. The error signal is combined in a summing junction with a command signal to correct an actuator, such as beam/tube positioner 52. Corrections are continued until the Raman scatter or fluorescence signals are maximized, thus achieving desired alignment.

Automation may also be accomplished by oscillating or dithering the translation or rotation of lens 20. This superimposes an oscillation onto the signals. The oscillating mechanism is also capable of a slower transition or rotation. The amplitude of the translation or rotation of lens 20 should be such as to produce about a 5% modulation of the detected signal. If the modulation is not symmetrical, the translation or rotation mechanism should shift beam 15 a small amount in the direction of the larger signal. In this way, the system continually hunts for the lens position producing the largest signal. The frequency of modulation should be significantly higher than the fundamental frequency of signal change caused by migration of sample components down capillary tube 10.

As stated earlier, capillary tube 10 contains a matrix that results in Raman scatter signals, according to the present invention. This matrix need not be the target sample which is to be analyzed by fluorescence detection. If the matrix is simply an electrophoretic separation gel, e.g., the Raman scatter signals emitted from the detection region are used for tube-and-beam alignment and the fluorescence signals emitted by the gel alone may be low. When the target sample passes through tube 10, however, as by electrophoresis, the fluorescence signals emitted may be more useful for analysis purposes.

Figure 6:
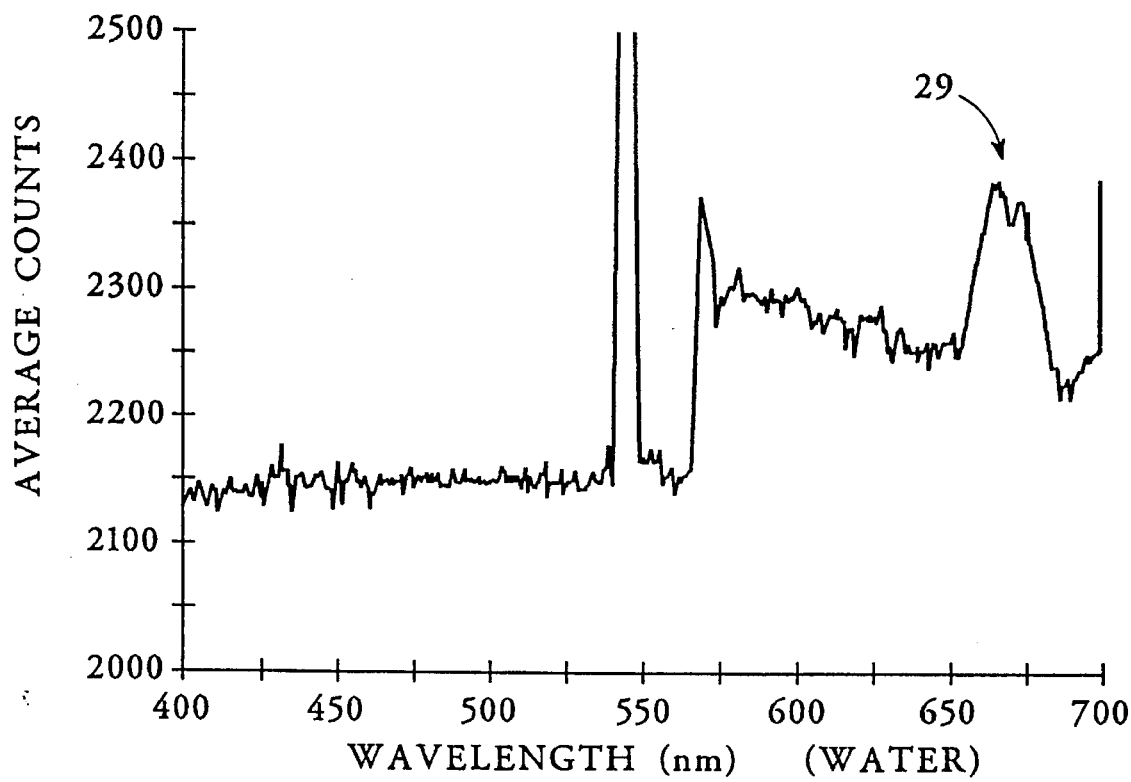
FIG. 6 is a graphic representation of the 400 to 700 nm spectrum of a water-filled capillary tube according to the present invention.
Figure 7:
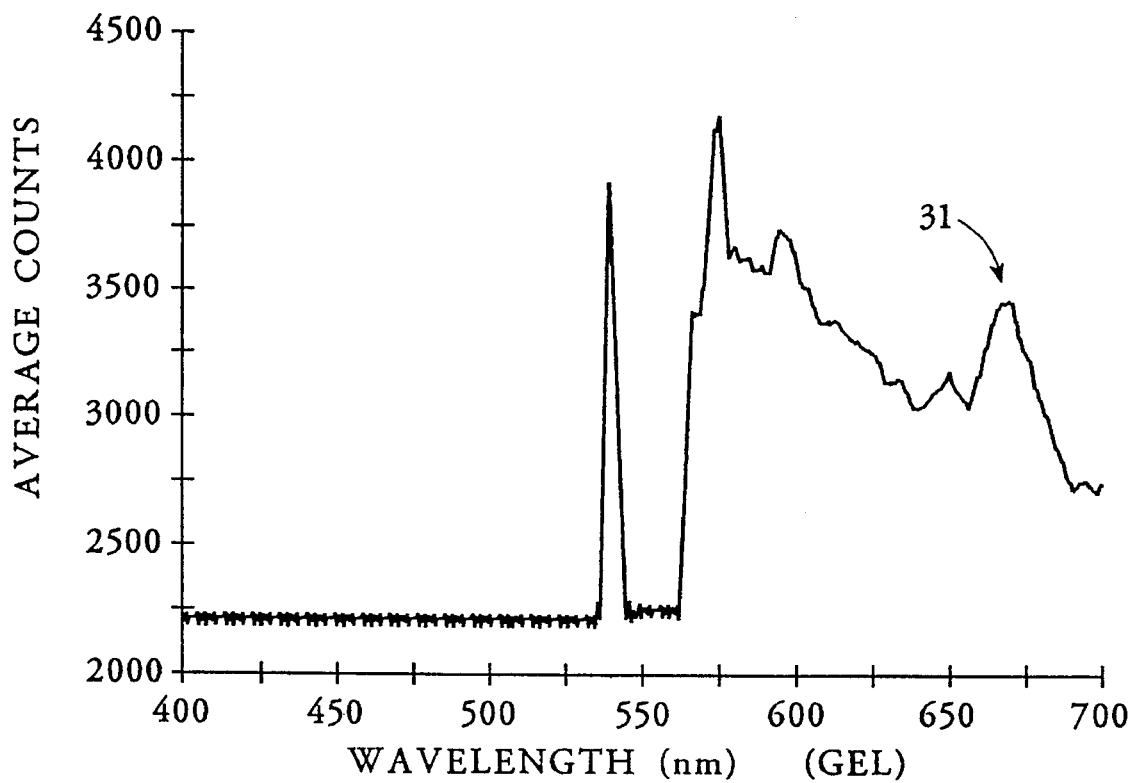
FIG. 7 is a graphic representation of the 400 to 700 nm spectrum of a gel-filled capillary tube according to the present invention.

FIG. 6 depicts a spectrum from 400 to 700 nm for a water-filled 50 µm interior diameter capillary tube held in reflector 25 of FIG. 1. Excitation beam 15 has its source, in this case, at a 543.5 nm Helium-Neon laser. To obtain this spectrum, the output of reflector 25 was imaged upon the entrance slit of a grating and a CCD detector was placed at the exit slit of the grating. The broad band 29, centered at 665 nm of FIG. 6, is due to Raman scattering by the tube's contents. The intensity of band 29 decreases as beam 15 is translated away from optimum in either the Y- or Z-direction. When band 29 is properly intensified by movement of lens 20, then beam 15 and tube 10 are accurately aligned for optical detection of fluorescence or other signals. FIG. 7 depicts a similar spectrum from 400 to 700 nm for a linear polyacrylamide gel-filled capillary tube. The Raman scattering of the gel matrix is visible at band 31, centered at 665 nm.

In the practice of the present invention, both Raman scatter and fluorescence emission signals are detected when no rotating filter is in the path of the collimated detected beam, e.g. sector 34 of FIG. 3B is in the detected signal's path. When a fluorescent sample migrates through tube 10 to its intersection point with beam 15, the detected signal will have a spectrum corresponding to the superposition of Raman and fluorescence spectra. Either signal may be used for alignment, but it is often desirable to distinguish between the two types of signals. If the fluorescence spectrum has no significant component at wavelengths longer than approximately 650 nm, then fluorescence emission and Raman scatter signals are distinguishable by choosing the appropriate sector of filter wheel 17.

Use of a dispersive element and an array-type detector, as mentioned above, permits simultaneous monitoring of both the fluorescence and Raman signals. This would allow dynamic alignment during the analytical run and would also provide Raman scatter signals which would reflect certain characteristics of the source, such as polarization and power stability, while the fluorescence signal from the sample would be variable as the separation progressed. The Raman scatter signals could then serve as the underlying feedback signal source for auto-alignment or provide a polarization reference.

Figure 8A:
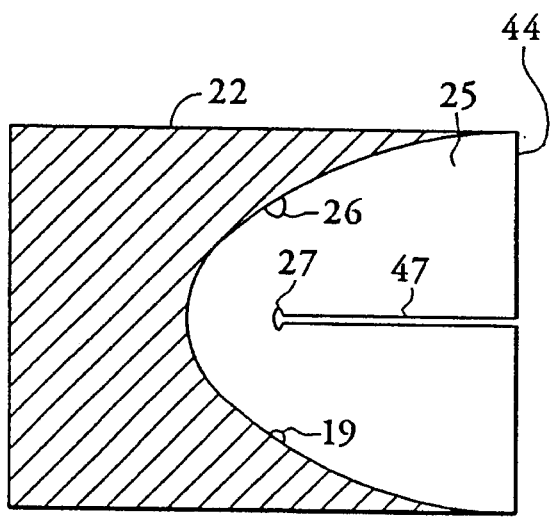
FIGS. 8A–8B show side views of the parabolic reflector of the present invention in a fitted holder, the reflector of 8A having rim slots and the reflector of 8B having a bowl slot.
Figure 9A:
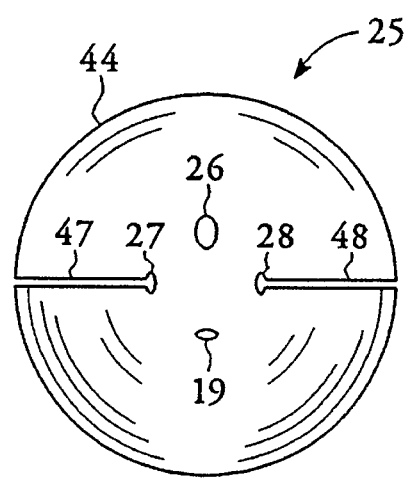
FIGS. 9A–9B show end views of the parabolic reflector of the present invention, the reflector of 9A having rim slots and the reflector of 9B having a bowl slot.
Figure 8B:
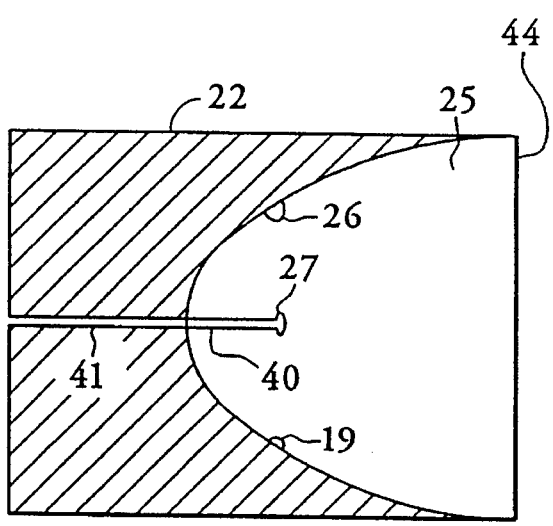
Figure 9B:
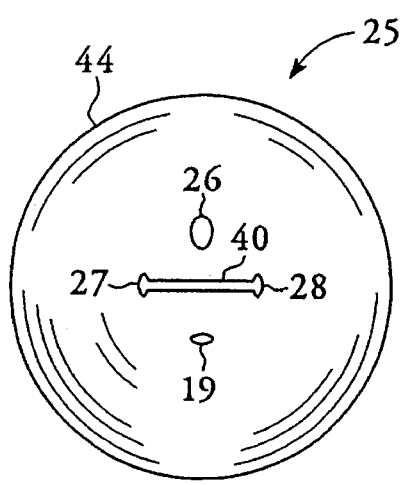

In some experimental formats, it may be desirable to keep a capillary tube stationary, which may make guiding the tube through the parabolic reflector quite difficult. This problem is resolved by effectively extending the tube apertures 27 and 28 to the rim of the reflector with slots 47 and 48, as shown in FIGS. 8A and 9A, in side and end views, respectively. Thus, the set of tube guides includes apertures and slots and the parabolic reflector may be pushed into place around a fixed position capillary tube. In other words, the tube apertures are accessible to the capillary tube from the rim of the reflector through slot 47, which connects tube entrance aperture 27 to rim 44, and through slot 48, which connects tube exit aperture 28 to rim 44. The capillary tube itself is not illustrated in FIGS. 8A–B and 9A–B. FIGS. 8B and 9B show an alternative means of allowing access by a fixed position capillary tube to the tube apertures of the reflector. A single slot 40 is defined in the wall of reflector 25 along the bowl, extending from tube entrance aperture 27 to tube exit aperture 28. In the case of a bowl slot, the reflector is pushed into place around the capillary tube from its back end, i.e. the end opposite the rim. If a fitted holder 22 or similar holder is used with a bowl-slotted reflector, it may be necessary to also put a means of access for the capillary tube through the holder, as with slot 41 through fitted holder 22 in FIG. 8B. In FIGS. 8B and 9B, the set of tube guides of the present invention includes tube apertures 27 and 28 and slot 40. Creating narrow slots in the reflector does not lead to any significant loss of reflective surface or collimating ability of the reflector. If desired, slots may also be used in conjunction with the beam apertures.

Figure 10:
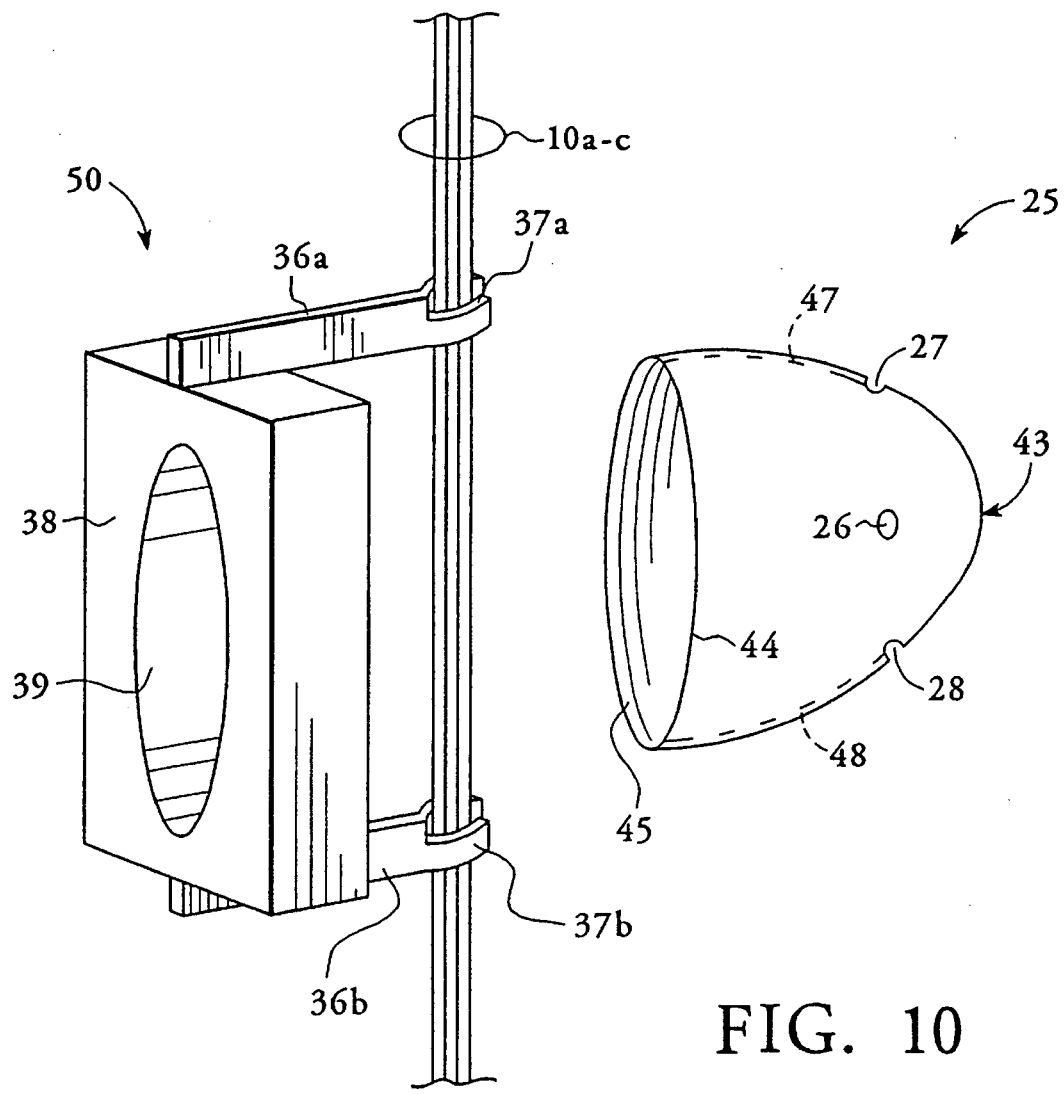
FIG. 10 shows a perspective view of the parabolic reflector of the present invention and a C-shaped holder for positioning an array of capillary tubes within the reflector.

With reference to FIG. 10, another variation of the optical alignment assembly and method of the present invention is shown. C-shaped holder 50 is an array-holder and comprises a block 38 with attached projection arms 36a–b. Projections 36a–b each contain clamps 37a–b, for gripping an array of capillary tubes 10a–c. A one-dimensional array of capillary tubes which adjoin lengthwise is generally most useful in the practice of the present invention. FIG. 10 shows the tube array 10a–c used in conjunction with a reflector that may be rim-slotted, as described above with regard to FIGS. 8A and 9A. A hole 39, at least the size of the open end of reflector 25 to prevent interference with the optical signals, is provided in C-shaped holder 50 when the holder is used at the front end of reflector 25. The hole is unnecessary if C-shaped holder 50 is used to position the array in reflector 25 from the back end of the reflector, as would be likely if the bowl slot of FIGS. 8B and 9B were the most useful configuration for the set of tube guides in the reflector. Slots in the reflector are not a requirement for alignment of an array with an excitation beam according to the present invention, provided the tube apertures are sufficiently large to accommodate the array and the capillary tubes themselves are not immobile. C-shaped holder 50 is positioned about reflector 25 and supports passage of the array through the reflector via the set of tube guides.

Tube array 10a–c is positioned to enter the slots single file, i.e. in series with respect to the central axis of reflector 25, in FIG. 10. This allows for sequential alignment of the tubes with a fluorescence excitation beam. The beam 15 is directed through lens 20 and beam apertures 19 and 26 to sequentially intersect with each tube of array 10a–c. As each detection region is illuminated by beam 15, the Raman scatter signals are collected and used for alignment, as with the single tube arrangement. The fluorescence signals may be collected from each tube while the Raman scatter signals are maximized, as before.

It is also possible to position the tube array so that the tubes are gripped in a side-by-side format by the projections 36a–b of C-shaped holder 50. In other words, the tube array is arranged in parallel with respect to the central axis of reflector 25 and multiple tubes may enter the slots simultaneously. Tube apertures and slots may need to be wider to accommodate this type of array. For this type of arrangement, fluorescence beam excitation through the side beam apertures of the reflector, described above, is impractical. Therefore, alternate embodiments of the optical system of the present invention are desired.

Figure 11:
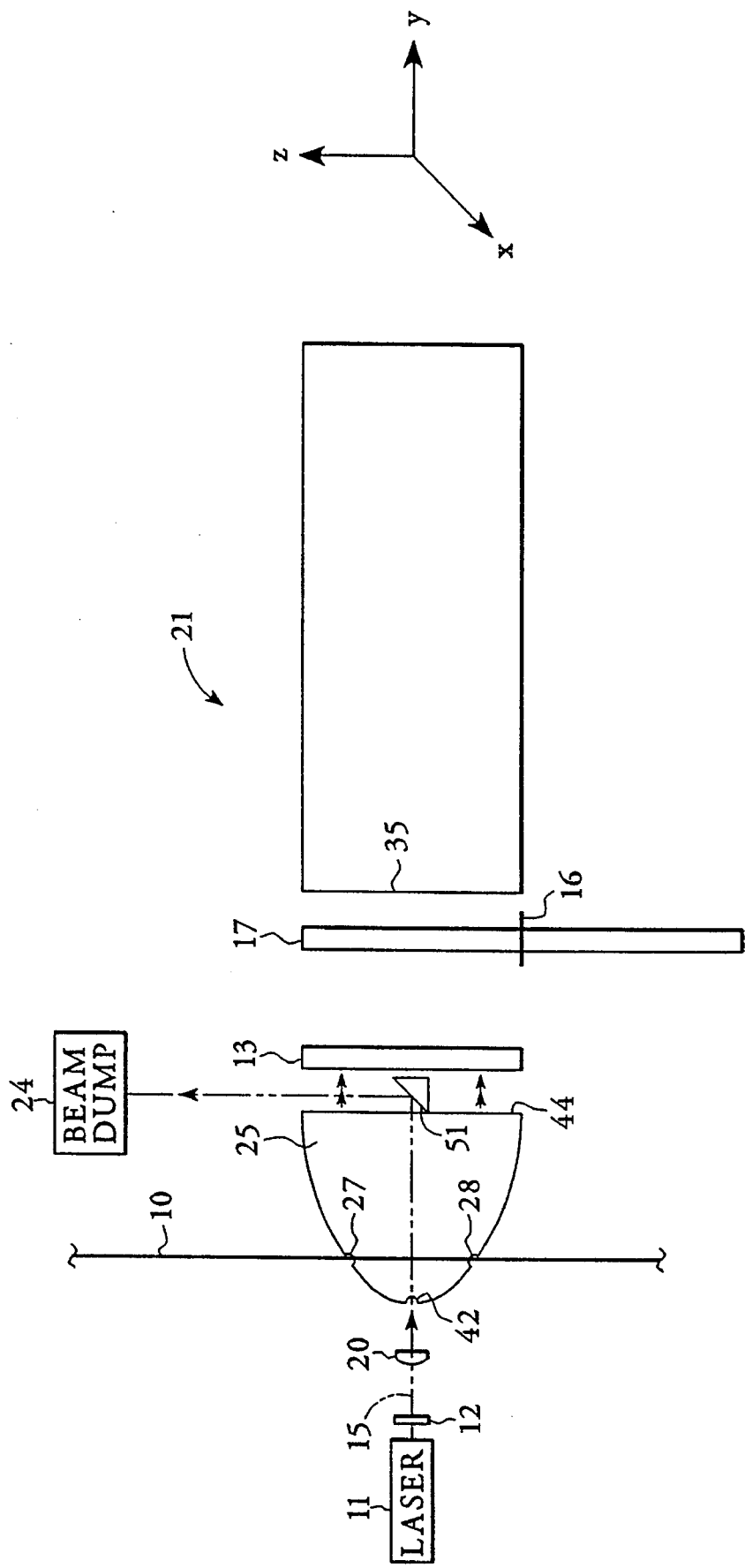
FIG. 11 is an alternate embodiment of the optical system of the present invention.
Figure 12:
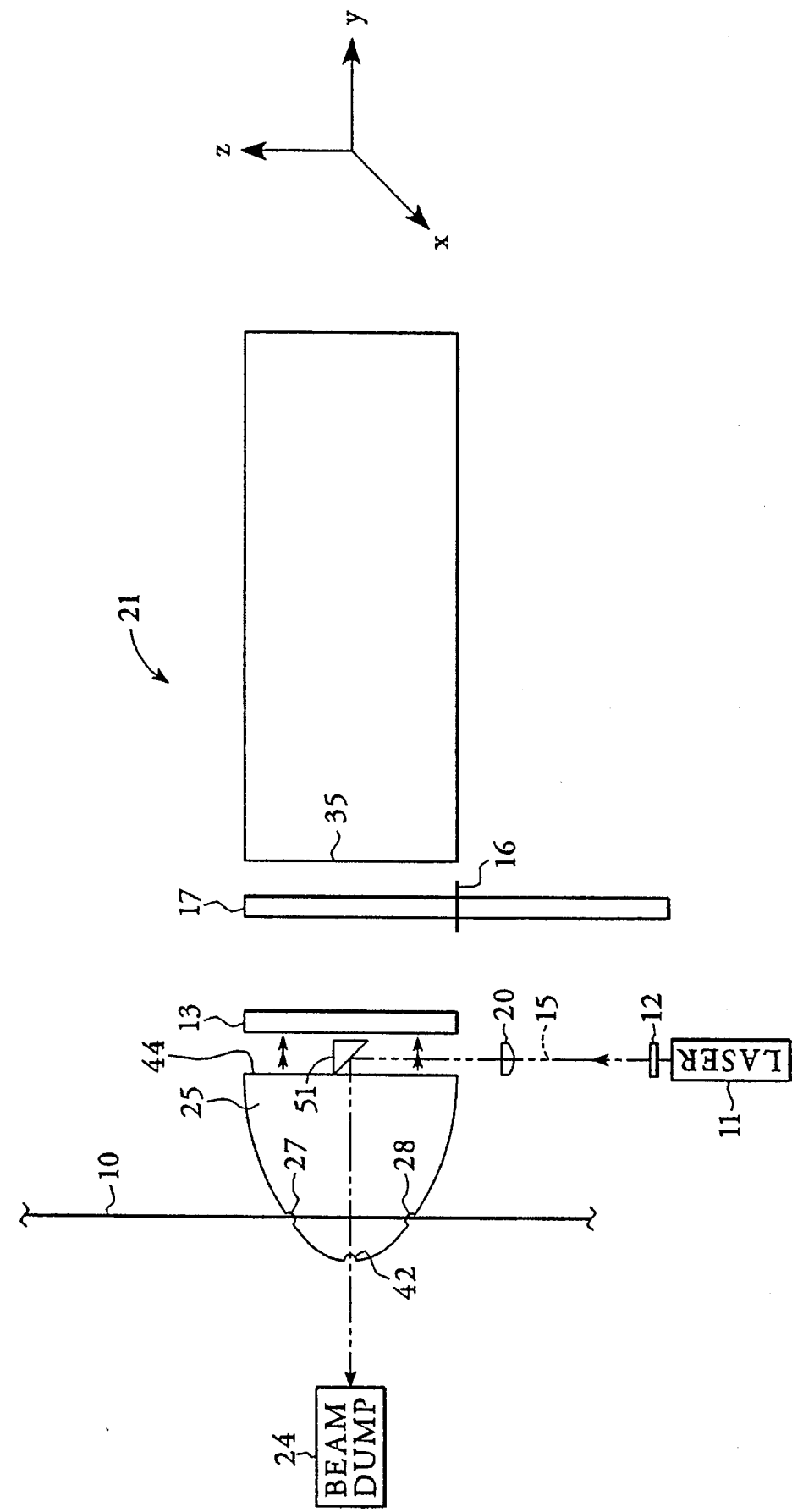
FIG. 12 is yet another alternate embodiment of the optical system of the present invention.

FIGS. 11 and 12 present alternate embodiments, which are most useful with a capillary tube array that is arranged in parallel with respect to the central axis of reflector 25. The beam guide means defined in the reflector of the present invention is a single beam aperture through the vertex of reflector 25 for these embodiments, instead of a pair of beam apertures through the side of the reflector. The vertex aperture 42 is shown in FIG. 11 and is used to direct beam 15 through the bottom of reflector 25 to intersect capillary tube 10 within the reflector, preferably at 90° angles and preferably at focal point 30, as before. This bottom-excitation embodiment requires removal of the strong excitation beam 15, however, from the path leading generally along the central axis of reflector 25 to the detector. Reflective wedge 51, positioned proximate to rim 44 and in the path of beam 15, serves to redirect beam 15 away from the detection optics and towards beam dump 24, in the embodiment of FIG. 11. Wedge 51 also serves as a scatter block, similar to scatter block 18 of the preferred embodiment, in the embodiments of FIGS. 11 and 12.

FIG. 12 is yet another embodiment showing the fluorescence excitation beam 15 intersecting capillary tube 10 from the direction of the open end of reflector 25. After intersecting tube 10, beam 15 passes through vertex aperture 42 and to beam dump 24. As with the FIG. 11 embodiment, reflective wedge 51, proximate to rim 44, serves to direct the path of beam 15 relative to the central axis of reflector 25. Sequential alignment of a one-dimensional, side-by-side or parallel-arranged capillary tube array with a fluorescence excitation beam is easiest with the optical configuration depicted in FIGS. 11 and 12, because of the relative directions of the tube and the beam.

Although the present invention adapts readily to fluorescence detection in the capillary electrophoresis context, the invention may be used for other applications requiring optical alignment, as well. For example, the invention may be used for chromatography or in fluorescence assays. In addition, proper alignment may be needed for detection optics with respect to sample tubes, cuvettes and holders or cells having small detection regions.

The present invention employs information always available in a laser-induced fluorescence system. Raman scattering is easily correlated with any matrix and laser combination. The process and system of the present invention are fully automatable and represent an important advance in the art because the use of fluorescent material is not required to accomplish optical alignment. In addition, the apparatus of the present invention employs a single detector for both analytical measurement of the sample and fine adjustment of the optical alignment system, which is an important improvement in terms of both the simplicity of the invention's design and the cost of implementation.

We claim:

1. An optical alignment assembly for fluorescence detection, utilizing a capillary tube, comprising
   an axially symmetrical concave reflector having a wall bounded by a rim, a bowl opposite the rim incorporating a vertex, a focal region, a set of tube guides defined by the wall, the tube guides allowing passage of the capillary tube through the reflector, and a beam guide means defined by the wall for directing an excitation beam such that a path of the beam intersects with the capillary tube within the reflector, a region of intersection emitting Raman scatter signals, means disposed for collecting and detecting the Raman scatter signals, and means connected to the detecting means for adjusting position of the beam relative to the capillary tube to maximize the detected Raman scatter signals.

2. The assembly of claim 1 wherein the means for adjusting the position of the beam is in continuous communication with the detecting means, whereby the beam position may be adjusted relative to the capillary tube during fluorescence detection to maintain the Raman scatter signals at their maximum.

3. The assembly of claim 2 wherein the means for adjusting is a closed loop servo system.

4. The assembly of claim 2 wherein the means for adjusting is a means for dithering the beam relative to the capillary tube.

5. The assembly of claim 1 wherein the means for adjusting the position of the beam comprises a lens for focusing the beam into the capillary tube, the lens positioned exterior to the reflector and in the path of the beam before it intersects the capillary tube, and a positioner in communication with the lens and the detecting means for shifting the lens in response to a signal received from the detecting means.

6. The assembly of claim 5 wherein the lens is a plano-convex lens oriented so that the beam enters the lens at a convex surface and exits the lens at a planar surface.

7. The assembly of claim 1 wherein the axially symmetrical concave reflector comprises a parabolic reflector.

8. The assembly of claim 1 wherein the focal region of the reflector comprises a focal point and a focal plane.

9. The assembly of claim 8 wherein the capillary tube is passed through the tube guides such that the capillary tube crosses the focal point of the reflector.

10. The assembly of claim 9 wherein the excitation beam is directed such that the beam intersects with the capillary tube at the focal point of the reflector.

11. The assembly of claim 8 wherein the set of tube guides defined in the reflector includes a tube entrance aperture and a tube exit aperture, the tube apertures positioned near the focal plane of the reflector, the tube entrance aperture positioned approximately 180° along the wall from the tube exit aperture.

12. The assembly of claim 11 wherein the beam guide means defined by the reflector includes a beam entrance aperture and a beam exit aperture, the beam apertures positioned near the focal plane of the reflector, the beam entrance aperture positioned approximately 180° along the wall from the beam exit aperture.

13. The assembly of claim 12 wherein the beam entrance aperture is positioned approximately 90° along the wall from the tube entrance aperture, whereby the capillary tube may be guided through the reflector via the tube entrance and exit apertures and the excitation beam may be directed through the reflector via the beam entrance and exit apertures to cause intersection of the capillary tube and the beam at approximately 90° angles.

14. The assembly of claim 11 wherein the beam guide means defined by the reflector includes a vertex aperture, the vertex aperture positioned at the vertex of the reflector, whereby the capillary tube may be guided through the reflector via the tube entrance and exit apertures and the excitation beam may be directed through the vertex aperture to cause intersection of the capillary tube and the beam at approximately 90° angles.

15. The assembly of claim 11 wherein the tube entrance aperture and the tube exit aperture are accessible to the capillary tube from the rim of the reflector by a pair of slots defined in the reflector, the first slot of the pair extending from the tube entrance aperture to the rim and the second slot of the pair extending from the tube exit aperture to the rim.

16. The assembly of claim 11 wherein the tube entrance aperture and the tube exit aperture are accessible to the capillary tube from the bowl of the reflector by a slot defined in the reflector, the slot extending along the bowl from the tube entrance aperture to the tube exit aperture.

17. The assembly of claim 1 further comprising an array-holder positioned about the reflector for holding an array of capillary tubes and supporting passage of the array through the reflector via the set of tube guides defined by the wall of the reflector.

18. The assembly of claim 17 wherein the array-holder comprises a C-shaped holder, the array being gripped by projections of the C-shaped holder.

19. The assembly of claim 18 wherein the projections of the C-shaped holder grip the array so that the capillary tubes adjoin lengthwise and are arranged in series with respect to the central axis of the reflector.

20. The assembly of claim 18 wherein the projections of the C-shaped holder grip the array so that the capillary tubes adjoin lengthwise and are arranged in parallel with respect to the central axis of the reflector.

21. The assembly of claim 1 wherein the means for collecting and detecting the Raman scatter signals comprises a scatter block for passage of Raman scatter and fluorescence signals and obstruction of a substantial portion of Rayleigh scattering and reflections surrounding the capillary tube, the scatter block intersecting the central axis of the reflector proximate to the rim of the reflector, a longpass filter for attenuating any Rayleigh scattering and reflections that bypassed the scatter block, a rotating filter wheel positioned to receive the signals passing through the long pass filter and having means for passing the Raman scatter signals, and a detector responsive to the Raman scatter signals received from the filter wheel.

22. The assembly of claim 21 wherein the scatter block is an opaque strip aligned with the beam path.

23. The assembly of claim 21 wherein the scatter block is a reflective wedge, the wedge positioned to direct the excitation beam path relative to the central axis of the reflector.

24. The assembly of claim 21 wherein the rotating filter wheel comprises a first sector having a first band pass filter for passing fluorescence signals, and a second sector having a second band pass filter for passing Raman scatter signals.

25. The assembly of claim 21 wherein the rotating filter wheel comprises a first sector having a band pass filter for passing fluorescence signals, and a second sector having no filter.

26. The assembly of claim 21 wherein the detector is a photomultiplier tube.

27. The assembly of claim 21 wherein the detector is an array-type detector.

28. A method for aligning a fluorescence excitation beam and a capillary tube comprising providing a parabolic reflector having a wall bounded by a rim, a bowl opposite the rim incorporating a vertex, and a focal region incorporating a focal plane and a focal point, defining a set of oppositely-spaced tube guides near the focal region and a beam guide means through the wall of the reflector, guiding a capillary tube containing a matrix through the set of tube guides, directing an excitation beam through a focusing lens and then through the beam guide means to cause intersection of the capillary tube and the excitation beam at the focal region within the reflector, thereby forming a detection region with Raman scatter and fluorescence signals being emitted from the detection region, collecting and detecting the Raman scatter signals, shifting the relative positions of the beam and the capillary tube to maximize the Raman scatter signals, and then collecting and detecting the fluorescence signals.

29. The method of claim 28 wherein the step of shifting the relative positions of the beam and the capillary tube is automated and occurs continuously in conjunction with detection of the Raman scatter signals so that the Raman scatter signals remain maximized.

30. The method of claim 28 wherein the step of guiding a capillary tube comprises positioning the capillary tube so that it passes through the focal point of the reflector.

31. The method of claim 30 wherein the step of directing an excitation beam comprises directing the beam to intersect the capillary tube at the focal point of the reflector.

32. The method of claim 28 wherein the step of directing an excitation beam further comprises directing the beam to intersect the capillary tube at approximately 90° angles.

33. The method of claim 28 wherein the step of defining a set of oppositely-spaced tube guides comprises positioning a pair of tube apertures in the wall near the focal plane of the reflector.

34. The method of claim 33 wherein the step of defining a beam guide means comprises positioning a set of oppositely-spaced beam apertures in the wall near the focal plane of the reflector.

35. The method of claim 33 wherein the step of defining a beam guide means comprises positioning a beam aperture in the vertex of the reflector.

36. The method of claim 33 wherein the step of defining a set of oppositely-spaced tube guides further comprises defining a pair of slots in the wall of the reflector, each slot extending from the rim of the reflector to one of the tube apertures.

37. The method of claim 33 wherein the step of defining a set of oppositely-spaced tube guides further comprises defining a slot in the wall of the reflector, the slot extending between the tube apertures along the bowl of the reflector.

38. The method of claim 28 wherein the step of directing an excitation beam through a focusing lens further comprises orienting a plano-convex focusing lens so that the beam enters the lens at a convex surface and exits the lens at a planar surface.

39. The method of claim 28 further comprising passing a target sample through the capillary tube after shifting the position of the lens to maximize the Raman scatter signals and before collecting and detecting the fluorescence signals.

40. A method for aligning a fluorescence excitation beam and a capillary tube comprising providing a parabolic reflector having a wall and a focal region, defining a set of oppositely-spaced tube guides through the wall of the reflector near the focal region and a beam guide means through the wall of the reflector, guiding a capillary tube containing a matrix through the set of tube guides, directing an excitation beam through a focusing lens and then through the beam guide means to cause intersection of the capillary tube and the excitation beam within the reflector, thereby forming a detection region with Raman scatter and fluorescence signals being emitted from the detection region, simultaneously collecting and detecting the Raman scatter and fluorescence signals with a dispersive element and an array-type detector, and shifting the position of the lens to maximize the Raman scatter signals and thereby align the beam and the capillary tube while collecting and detecting the Raman scatter and fluorescence signals.

41. A method for sequentially aligning a fluorescence excitation beam and each capillary tube in a one-dimensional array of capillary tubes, the method comprising providing a parabolic reflector having a wall and a focal region, defining a set of oppositely-spaced tube guides through the wall of the reflector near the focal region and a beam guide means through the wall of the reflector, guiding a one-dimensional array of matrix-containing capillary tubes through the set of tube guides, directing an excitation beam through a focusing lens and then through the beam guide means to sequentially intersect within the reflector with each of the capillary tubes of the array, thereby forming a detection region in each of the capillary tubes with Raman scatter and fluorescence signals being emitted from each of the detection regions, collecting and detecting the Raman scatter signals from each detection region while the excitation beam intersects each of the capillary tubes, shifting the position of the lens to maximize the Raman scatter signals from each detection region while the excitation beam intersects each of the capillary tubes, and collecting and detecting the fluorescence signals from each detection region while the Raman scatter signals are maximized.

42. An automated optical alignment system for fluorescence detection comprising a parabolic reflector having a wall, a vertex, a focal plane incorporating a focal point, a set of oppositely-spaced tube guides defined by the wall for guidance of a capillary tube containing a matrix through the reflector, and a beam guide means defined by the wall for guidance of a fluorescence excitation beam through the reflector transverse to the guided tube to intersect the guided tube, the guided beam causing emission of Raman scatter signals from the region of intersection, a lens disposed exterior to the reflector for focusing the guided beam into the guided tube, an automated positioner for shifting the relative positions of the guided tube and the guided beam, and means for collecting and detecting the Raman scatter signals from the region of intersection of the guided tube and the guided beam, the means for collecting and detecting the Raman scatter signals being in communication with the positioner in order to shift the relative position of the guided tube and the guided beam as necessary to maximize the Raman scatter signals, thereby aligning the guided tube and the guided beam for fluorescence detection.

43. The alignment system of claim 42 wherein the automated positioner is in communication with the lens for shifting the guided beam relative to the guided tube.

44. The alignment system of claim 42 wherein the set of oppositely-spaced tube guides comprises a pair of tube apertures defined by the wall near the focal plane of the reflector.

45. The alignment system of claim 44 wherein the beam guide means comprises a pair of oppositely-spaced beam apertures defined by the wall near the focal plane of the reflector.

46. The alignment system of claim 44 wherein the beam guide means comprises a vertex aperture defined in the wall at the vertex of the reflector.

47. The alignment system of claim 42 further comprising means for positioning an array of capillary tubes through the reflector via the set of tube guides defined by the wall of the reflector, and means for directing the guided beam to sequentially intersect each capillary tube of the array.

48. Art automated optical alignment system for fluorescence detection comprising a parabolic reflector having a wall, a focal region, a set of oppositely-spaced tube guides defined by the wall for guidance of a capillary tube containing a matrix through the reflector, and a beam guide means defined by the wall for guidance of a fluorescence excitation beam through the reflector transverse to the guided tube to intersect the guided tube, the guided beam causing emission of fluorescence signals from the region of intersection, an automated positioner for shifting the relative positions of the guided tube and the guided beam, and means for collecting and detecting the fluorescence signals from the region of intersection of the guided tube and the guided beam, the means for collecting and detecting the fluorescence signals being in communication with the positioner in order to shift the relative positions of the guided tube and the guided beam to maximize the fluorescence signals.

* * * * *